United States Patent [19]

Lehto

[11] Patent Number: 4,597,027
[45] Date of Patent: Jun. 24, 1986

[54] CAPACITIVE PRESSURE DETECTOR STRUCTURE AND METHOD FOR MANUFACTURING SAME

[75] Inventor: Ari Lehto, Helsinki, Finland

[73] Assignee: Vaisala Oy, Helsinki, Finland

[21] Appl. No.: 741,473

[22] Filed: Jun. 5, 1985

[30] Foreign Application Priority Data

Jun. 7, 1984 [FI] Finland .................................. 842307

[51] Int. Cl.⁴ ........................... H01G 7/00; G01L 9/12
[52] U.S. Cl. .................................... 361/283; 29/25.42; 73/718
[58] Field of Search .................. 73/718, 724; 361/320, 361/283

[56] References Cited

U.S. PATENT DOCUMENTS

| 2,438,592 | 3/1948 | White | 29/25.42 X |
| 2,868,894 | 1/1959 | Schultz | 361/283 X |
| 4,257,274 | 3/1981 | Shimaoa et al. | 73/718 |
| 4,360,955 | 11/1982 | Block | 29/25.42 |
| 4,405,970 | 9/1983 | Swindal et al. | 361/283 |
| 4,424,713 | 1/1984 | Kroninger et al. | 73/718 |

FOREIGN PATENT DOCUMENTS 2059071  4/1981  United Kingdom ................. 73/724

Primary Examiner—Donald A. Griffin
Attorney, Agent, or Firm—Birch, Stewart, Kolasch & Birch

[57] ABSTRACT

Described herein are a capacitive pressure detector, with an electrically conductive substrate (1), an electrically conductive, plate-like member (3) disposed at a distance from the substrate, and an electrically insulating layer (2') hermetically bonding together the substrate (1) and the member (3) such that a capacitor chamber is formed between the substrate (1) and the member (3), as well as a method for manufacturing same. The method comprises machining at least one recess (5) into one side of the substrate (1), applying a layer (2) of electrically insulating material in molten state onto the machined side of the substrate (1) such that the layer (2) covers the machined side of the substrate, allowing the layer (2) to harden, removing material out of the surface of the structure in this way produced for obtaining a substantially plane surface with at least one conductive mesa portion (6) of the substrate (1) surrounded by at least one insulating layer portion (2').

8 Claims, 5 Drawing Figures

CAPACITIVE PRESSURE DETECTOR STRUCTURE AND METHOD FOR MANUFACTURING SAME

BACKGROUND OF THE INVENTION

The present invention concerns a capacitive pressure detector. The invention also concerns a method for manifacturing such a detector.

In respect of the prior-art technology, reference is made to the following papers:

[1] C. S. Sander, J. W. Knutti, J. D. Meindl, *IEEE Transactions on Electron Devices* Vol ED-27 (1980) No. 5, pp. 927–930
[2] U.S. Pat. No. 4,261,086
[3] U.S. Pat. No. 4,386,453
[4] U.S. Pat. No. 4,384,899
[5] U.S. Pat. No. 4,405,970
[6] U.S. Pat. No. 3,397,278.

In cited publication [1], a capacitive detector of absolute pressure is described, which consists of an elastic element of silicon and of a glass plate, which have been attached to each other by means of the method of cited paper [6]. Between the elastic element and the glass plate, a cavity remains which functions as the vacuum capsule of the detector. Between the elastic element and a metal film placed on the glass plate, a capacitance dependent on the pressure is produced. An electrical connection to the metal film placed on the glass plate is obtained from outside the detector by means of a conductor prepared into the silicon by means of diffusion and having a type of conductivity different from that of the elastic element. A major drawback of this detector is the high and highly temperature-dependent depletion capacitance produced between the diffused conductor and the elastic element, which enters to the side of the pressure-dependent capacitance of the detector. The relative dynamism of the detector decreases, and its dependence on temperature increases.

In the cited publications [2], [3] and [4], a pressure detector construction similar to the above is described. The wiring thereof is, however, different. The wiring is made through a hole drilled into the glass, which is metal-coated inside. The hole is closed by melting metal (solder) into it. The wiring has no parasitic properties. The sealing of the holes are, however, rather inconvenient to carry out in mass production.

In cited publication [5], a detector is described in which support plates made of silicon and the elastic element are "glued" onto each other by means of a thin glass film, which is made by sputtering or by vacuum evaporation. By means of the thickness of the glass film, the distance between the capacitor plates is also controlled. It is a good aspect of the detector construction that the material of manufacture is almost completely of silicon. That guarantees a good temperature stability. The stray capacitances related to the glass joint, however, spoil the properties of the detector. By means of the above methods, the thickness of the glass can be, at the maximum, 10 μm, whose capacitance corresponds to an air gap of 2 μm. Thus, the role of the joint zone is dominating in the capacitance of the detector, unless the area of the detector is very large.

In the cited publication [5], a construction is also described in which a high glass wall separates the said two silicon pieces. In that case, there is no problem of stray capacitance. The dimensional accuracy of the air gap in the capacitor will, however, be poor.

The object of the present invention is to eliminate the drawbacks present in the prior-art technology described above and to provide a capacitive pressure detector of an entirely novel type as well as a method for manufacturing the same.

The invention is based on the idea that a layer of an insulating material, e.g. glass, is melted or cast onto a substrate of a machinable and conductive material, e.g., silicon. Thereby, the thickness of the insulation layer is higher on the recesses provided in the substrate than on other portions thereof. When the insulation layer (and the substrate, partly) are ground so that the topmost portions of the frame layer and the remaining portions of the insulation layer form a uniform plane face, an electric passing-through is provided that extends from the bottom face of the substrate layer to its top face and that is, at its top end, surrounded by an insulation layer. Through the electric passing-through, it is possible to make a mechanical passing through by machining a hole through the electric passing-through.

SUMMARY OF THE INVENTION

More specifically, the detector and the method in accordance with the invention are characterized by what is stated in the in the accompanying claims. The advantages are:

Firstly, a structure is obtained in which the parasitic capacitance between the elastic element and the silicon part of the substrate is far lower than the detector capacitance. Moreover, the dependence of the parasitic capacitance on the temperature is low.

Secondly, a structure is obtained that is hermetically closed and whose deformations as a result of variations of temperature are little.

Thirdly, the structure is characterized in that the distance between the capacitor plates, a few micrometers, is determined on the basis of the elastic element, and can consequently be made dimensionally precise.

Fourthly, it is characteristic of the structure that the capacitor plate closest to the substrate is located electrically outside the vacuum chamber without any additional operations.

Fifthly, a structure is obtained which is well suitable for mass production.

BRIEF DESCRIPTION OF THE DRAWINGS

The invention will be examined in the following in more detail with the aid of the exemplifying embodiment in accordance with the accompanying drawings.

DESCRIPTION OF PREFERRED EMBODIMENTS

Figure 1:
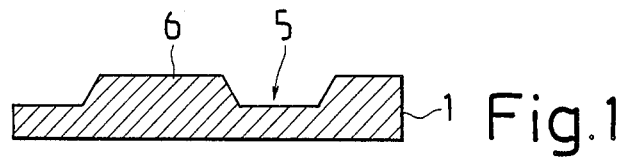
FIG. 1 is a cross-sectional view of a substrate blank made of a machinable, conductive material.
Figure 2:
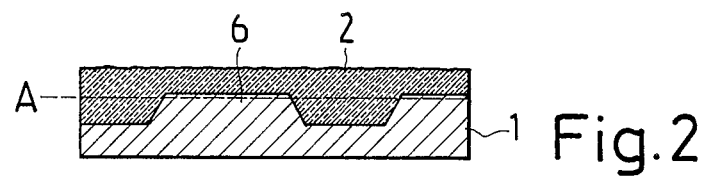
FIG. 2 shows a structure in accordance with FIG. 1, onto which a layer of insulating material has been cast.
Figure 3:
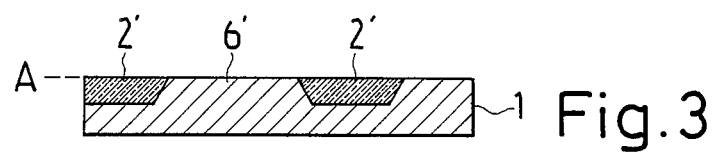
FIG. 3 shows the structure in accordance with FIG. 2 after its top face has been ground plane.
Figure 4:
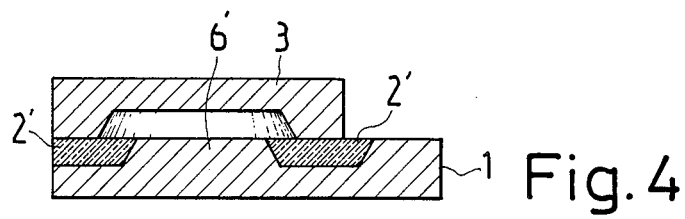
FIG. 4 shows a structure in accordance with FIG. 3, onto which a capsule made of a machinable material has been attached hermetically.
Figure 5:
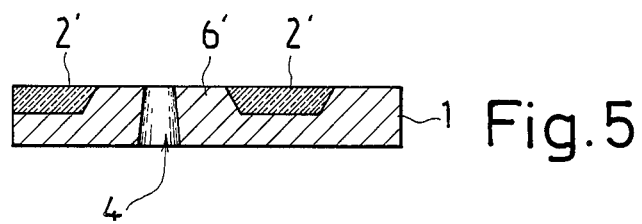
FIG. 5 shows a structure in accordance with FIG. 3 through whose wholly conductive portion a mechanical passing-through has been machined.

The silicon part 1 of the substrate is made of a silicon disc typically of a thickness of about 1.3 mm. The other dimensions are typically about 5×6 mm². The recess 5 is made by using prior-art silicon micromechanics so that its depth is about 200 μm. The area of the mesa-shaped zone 6 remaining in the middle is about 5 mm², and it forms one capacitor plate of the detector. The elastic element 3 which is sensitive to pressure forms the other capacitor plate. This must be attached to the substrate hermetically, but, at the same time, it must be insulated from it electrically. For this purpose, a glass layer 2 about 300 μm thick is melted onto the silicon part 1, as is shown in FIG. 2. For the glass, such a glass quality is chosen whose thermal expansion coefficient is close to that of silicon. Thereby, the deformations of the finished substrate owing to variations of temperature are at a minimum. Nor should the dielectric constant of the glass be strongly dependent on the temperature. Such glasses are, e.g., Corning 7740, 7070, and Schott 8248. After melting, the glass is ground off down to the level A, whereby the tops of the mesas 6 are also uncovered. Hereupon, the face is polished so well that the elastic element 4 can be attached to the glass 2', e.g., by anodic bonding, The electric contacts are made to the elastic element 3 and to the substrate 1, 2' by means of prior-art methods. The invention is as such suitable for an absolute detector, and for a differential detector if a hole 4 is made into the support plate in the way shown in FIG. 5.

The substrates 1, 2' may be made by sawing from a larger plate manufactured in the above way and having a diameter of, e.g., 7.6 cm. The silicon areas on the ground face A may be metal-coated by means of prior-art methods for the purpose of attaching external electric conductors to suitable locations. The hole 4 may be etched from below or from above, and its diameter may be 10 to 300 μm, as required, whereas the size of the top area of the mesa portion 6 is, in the example case, about 2 mm×2 mm.

The materials of the detector are preferably silicon and borosilicate glass. The detector is constructed in such a way that the plates of the capacitor sensitive to pressure are placed inside a vacuum capsule and are not in contact with the medium to be measured.

Due to the construction of the substrate, the capacitance between the capacitor plates inside the vacuum capsule can be measured from outside the detector. Hence, the dependence of the capacitance of the detector on the temperature can be made low.

Within the scope of the invention, it is also possible to conceive solutions differing from the above exemplifying embodiment. Thus, if necessary, onto the substrate, an insulation layer (not shown) may be produced by sputtering, depositing, etc. in order to prevent undesirable chemical reactions between the material to be cast and the substrate. As a result of such reactions, e.g., bubbles may be formed in the material to be cast. The insulation layer may be, e.g., a $SiO_2$ or $Si_3N_4$ layer of a, thickness of, e.g., 10 to 100 nm. This layer is, of course, ground off from the locations of the electric passing-through.

What is claimed is:

1. A capacitive pressure detector, comprising:
    a substrate made of an electrically conductive material and having an upper face including a first capacitor disc;
    an electrically insulating layer having an upper face and surrounding said first capacitor disc; and
    an electrically conductive elastic plate-like member hermetically bonded to the upper face of said electrically insulating layer and including a second capacitor disc such that a chamber is formed between said first and second capacitor discs;
    said electrically insulating layer being formed in a first recess made in said substrate, such that the upper faces of said substrate and said electrically insulating layer are substantially in the same plane and that said chamber is substantially formed as a second recess in that side of the plate-like member which faces said first capacitor disc.

2. A method for manufacturing a capacitive pressure detector with an electrically conductive substrate, an electrically conductive, plate-like member disposed at a distance from said substrate, and an electrically insulating layer hermetically bonding together said substrate and said member such that a capacitor chamber is formed between said substrate and said substrate and said member such that a capacitor chamber is formed between said substrate and said member, said method comprising the steps of:
    machining at least one recess into one side of said substrate;
    applying a layer of electrically insulating material in molten state onto said machined side of said substrate such that said layer covers the machined side of said substrate;
    allowing said layer to harden; and and
    removing material out of the surface of a structure in this way produced for obtaining a substantially plane surface with at least one conductive mesa portion of said substrate surrounded by at least one insulating layer portion.

3. Method as claimed in claim 2, wherein a silicon substrate is said substrate to be machined.

4. Method as claimed in claim 2, wherein is used as said insulating material.

5. Method as claimed in claim 2, wherein said layer of insulating material is cast onto the machined side of said substrate.

6. Method as claimed in claim 2, wherein said layer of insulating material is melted onto the machined side of said substrate.

7. Method as claimed in claim 2, wherein said layer of insulating material is allowed to cover said substrate completely.

8. Method as claimed in claim 2, wherein a mechanical passing-through is made by machining, e.g. etching, through said mesa portion.

* * * * *